(12) United States Patent
Lapham et al.

(10) Patent No.: US 8,681,334 B2
(45) Date of Patent: Mar. 25, 2014

(54) MEASUREMENT METHOD

(75) Inventors: Paul Lapham, Tyne and Wear (GB); Eric San Jose Robles, Newcastle upon (GB)

(73) Assignee: The Procter & Gamble Company, Cincinnati, OH (US)

(*) Notice: Subject to any disclaimer, the term of this patent is extended or adjusted under 35 U.S.C. 154(b) by 327 days.

(21) Appl. No.: 12/965,150

(22) Filed: Dec. 10, 2010

(65) Prior Publication Data

US 2011/0141474 A1 Jun. 16, 2011

(30) Foreign Application Priority Data

Dec. 10, 2009 (EP) .................................... 09178737

(51) Int. Cl.
*G01N 21/00* (2006.01)
*G01N 15/02* (2006.01)

(52) U.S. Cl.
USPC ........... 356/432; 356/335; 356/336; 356/337; 356/436; 356/441

(58) Field of Classification Search
None
See application file for complete search history.

(56) References Cited

U.S. PATENT DOCUMENTS

| | | | | |
|---|---|---|---|---|
| 2,379,158 | A * | 6/1945 | Kalischer | 356/442 |
| 3,283,644 | A * | 11/1966 | Saltzman | 250/565 |
| 5,246,779 | A * | 9/1993 | Heimberg et al. | 428/402 |
| 6,093,562 | A | 7/2000 | Bisgaard-Frantzen et al. | |
| 6,165,259 | A * | 12/2000 | Hallstrom et al. | 106/243 |
| 6,187,739 | B1 | 2/2001 | Merz et al. | |
| 6,331,512 | B1 | 12/2001 | Foote et al. | |
| 7,528,384 | B2 * | 5/2009 | Gratton et al. | 250/461.2 |
| 7,595,291 | B2 | 9/2009 | Bittner et al. | |
| 7,843,560 | B2 * | 11/2010 | Harner et al. | 356/243.2 |
| 7,879,154 | B2 | 2/2011 | Warkotsch et al. | |
| 2003/0004086 | A1 * | 1/2003 | Takana et al. | 510/445 |
| 2003/0186828 | A1 | 10/2003 | Holderbaum et al. | |
| 2003/0196278 | A1 * | 10/2003 | Durfee | 8/158 |
| 2006/0269501 | A1 * | 11/2006 | Johnson et al. | 424/70.13 |
| 2007/0148211 | A1 * | 6/2007 | Altreuter et al. | 424/441 |
| 2008/0188391 | A1 | 8/2008 | Seebeck et al. | |
| 2008/0216563 | A1 * | 9/2008 | Reed et al. | 73/61.71 |
| 2009/0183317 | A1 * | 7/2009 | Meier et al. | 8/137 |
| 2009/0308133 | A1 * | 12/2009 | Merchant et al. | 73/1.03 |
| 2010/0041574 | A1 | 2/2010 | Warkotsch et al. | |

(Continued)

FOREIGN PATENT DOCUMENTS

EP 0 629 690 A1 12/1994
EP 1 600 497 A1 11/2005

(Continued)

OTHER PUBLICATIONS

Barker G E and Kern C R: "A comparison two methods for testing detergents"; The journal of the American Oil Chemists' Society; vol. 27, No. 4, 1950, pp. 113-116, XP002565175.

(Continued)

*Primary Examiner* — Gordon J Stock, Jr.
(74) *Attorney, Agent, or Firm* — Abbey A. Lopez

(57) ABSTRACT

A method for quantifying the soil dispersion capacity of a cleaning product or component thereof where the method comprises the following steps:
a) making a solution comprising the cleaning product or component thereof;
b) adding the soil to the cleaning product or component thereof solution to form a mixture; and
c) measuring the light blocked by the mixture.

7 Claims, 1 Drawing Sheet

(56) References Cited

U.S. PATENT DOCUMENTS

| | | | |
|---|---|---|---|
| 2010/0110220 A1* | 5/2010 | Leugers et al. | 348/222.1 |
| 2010/0150850 A1* | 6/2010 | Tamor et al. | 424/59 |
| 2010/0154832 A1 | 6/2010 | Zipfel et al. | |
| 2010/0160204 A1 | 6/2010 | Zipfel et al. | |
| 2010/0209512 A1* | 8/2010 | Driscoll et al. | 424/489 |
| 2010/0261029 A1* | 10/2010 | Borysenko et al. | 428/562 |
| 2010/0294309 A1 | 11/2010 | Tropsch | |
| 2010/0305018 A1 | 12/2010 | Bittner et al. | |
| 2011/0139182 A1* | 6/2011 | Lapham et al. | 134/18 |
| 2011/0207647 A1* | 8/2011 | Preuschen et al. | 510/226 |
| 2011/0257298 A1* | 10/2011 | Ishihara et al. | 523/442 |
| 2012/0244288 A1* | 9/2012 | Young et al. | 427/385.5 |

FOREIGN PATENT DOCUMENTS

| | | |
|---|---|---|
| EP | 1 904 613 A1 | 4/2008 |
| JP | A-S62-100637 | 5/1987 |
| JP | A-H10-095749 | 4/1998 |
| JP | A-H10-226800 | 8/1998 |
| WO | WO 95/06873 | 3/1995 |
| WO | WO 00/37627 A1 | 6/2000 |
| WO | WO 02/068577 A1 | 9/2002 |
| WO | WO 2007/068920 A1 | 6/2007 |
| WO | WO 2008/035071 A1 | 3/2008 |
| WO | WO 2008/110816 A1 | 9/2008 |
| WO | WO 2010/031605 A1 | 3/2010 |

OTHER PUBLICATIONS

International Search Report 10 Pages of PCT/US2010/059425 received Mar. 3, 2011.

U.S. Appl. No. 12/965,074, filed Dec. 10, 2010, Anju Deepali Massey Brooker.

U.S. Appl. No. 12/965,095, filed Dec. 10, 2010, Anju Deepali Massey Brooker.

U.S. Appl. No. 12/965,119, filed Dec. 10, 2010, Anju Deepali Massey Brooker.

U.S. Appl. No. 12/965,132, filed Dec. 10, 2010, Paul Lapham.

* cited by examiner

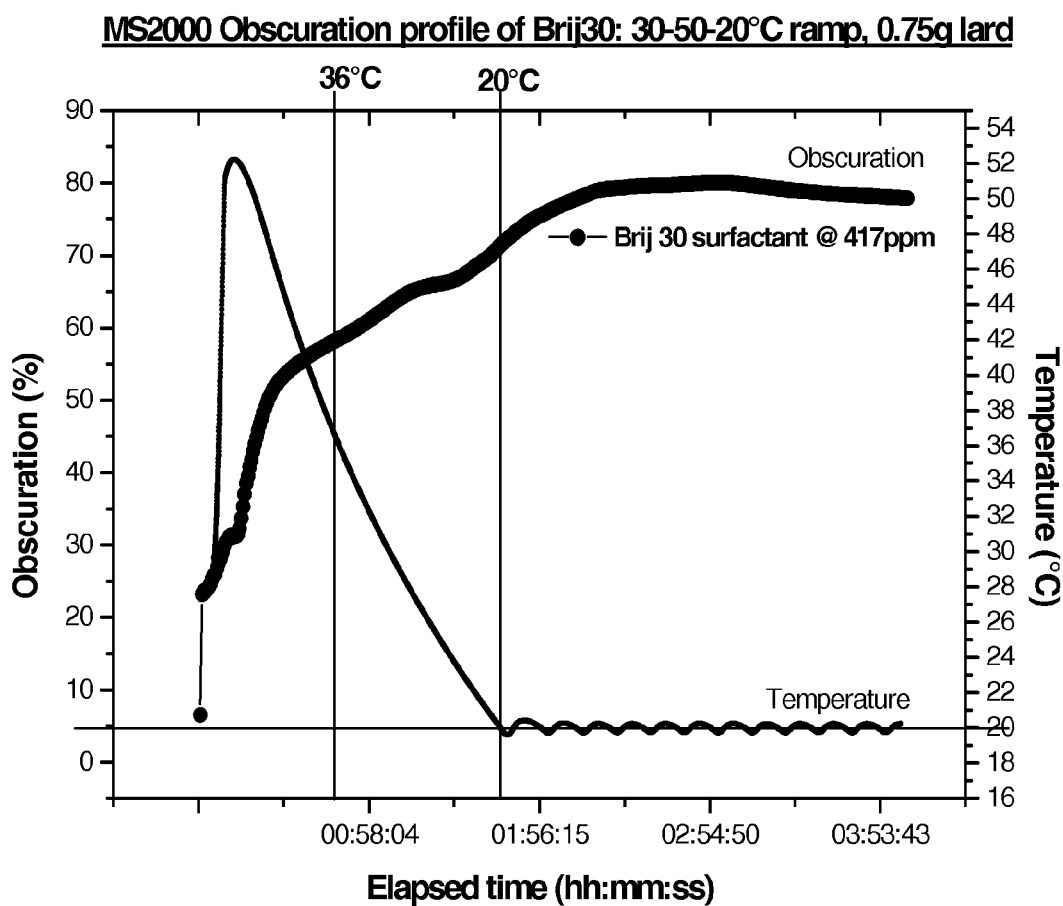

MEASUREMENT METHOD

TECHNICAL FIELD

The present invention is in the field of analytical measurements. In particular, it relates to a method for quantifying the soil dispersion capacity of a cleaning product or component thereof.

BACKGROUND

Detergent formulators are constantly trying to improve cleaning products. In order to assess the cleaning properties of a product it is desirable to quantify its soil removal capacity. This would help to minimise the amount of testing needed during product designs.

Hitherto there are no techniques available to consistently quantify soil removal of cleaning products and components thereof. Thus, the objective of the present invention is to provide a technique capable to quantify the soil removal capacity of a cleaning product and a component thereof. The present invention also tries to provide a technique that can be used to quantify the soil removal capacity of a cleaning product or components thereof under real conditions. For example, to evaluate a dishwashing detergent under the conditions found in an automatic dishwashing machine.

SUMMARY OF THE INVENTION

According to a first aspect of the invention, there is provided a method for quantifying (i.e., to measure quantitatively) the soil dispersion capacity of a cleaning product or a component thereof. The method comprises the following steps:
a) making a solution comprising the cleaning product or a component thereof;
b) adding the soil to the solution resulting from step a) to form a mixture; and
c) measuring the light blocked by the mixture.

The method of the invention allows quantify the soil dispersion capacity of a finished cleaning product (including personal cleansing, laundry, manual and automatic detergent, hard surface cleaners, etc) and also of components of the cleaning product such as surfactants, polymers, etc. The method is particularly suitable for measuring the soil dispersion capacity of surfactants.

Preferably the solution is an aqueous solution. When the soil is added to the solution of the cleaning product or component thereof, a dispersion is formed, the dispersion comprises cleaning product or cleaning component/soil in particulate form. The light blocked by the particles of the dispersion is measured. The measurements can be performed using any known technique, such as turbidity, absorbance, transmission, laser diffraction, etc. Preferably the light blocked by the mixture is quantified by measuring obscuration preferably using a particle size analyser based on laser diffraction.

The cleaning products to be assessed according to the method of the invention can comprise water-insoluble material (i.e., insolubles). In embodiments where this is the case, the method of the invention comprises the step of separating the insolubles, this can be done by any known means such as filtration.

In preferred embodiments the method of the invention comprises the step of measuring the light blocked by a solution of the cleaning product or component thereof and subtracting it to the light blocked by the mixture of the solution of the of the cleaning product or component thereof and the soil. This takes away the background noise due to the cleaning product or component thereof.

The method of the invention can be performed under simulated real life conditions, this is extremely relevant in cases in which the soil dispersion capacity of products and components thereof varies with different operation conditions, such as time, temperature, etc. This has been found particularly useful in the case in which the product is to be used in an appliance as for example an automatic dishwashing. What it is important is not the performance of a cleaning product at a fix point on time of the dishwashing process but the performance of the product over the whole dishwashing process. Thus, the method of the invention is extremely useful for the design of automatic dishwashing cleaning products.

In preferred embodiments the simulation of the appliance takes place in a temperature controlled vessel, adapted to simulate the working conditions of an appliance. A jacketed vessel has been found most suitable for use herein.

The method of the invention is particularly suitable for determining grease dispersing capacity of cleaning products or components thereof. It is also suitable for any other soils that are dispersed rather than dissolved in the presence of the cleaning product or component thereof to be measured. Especially for particulate soils. "Particulate" for the purpose of the invention includes droplets and materials in solid form whose particle size change during the cleaning process, such as clay, etc.

As indicated herein before the method is very well suited for determining the soil dispersing capacity of surfactants, in particular for determining the grease dispersing capacity.

BRIEF DESCRIPTION OF THE DRAWINGS

FIG. 1 is a graph related to the MS2000 obscuration profile of brig 30: 30-50-20° C. ramp, 0.75 grams lard which show the percent obscuration in relation to elapsed time.

DETAILED DESCRIPTION OF THE INVENTION

The present invention envisages a method for quantifying the soil dispersion capacity of a cleaning product or component thereof. The method can be performed simulating real life conditions and contributes to a simpler optimization of the design of cleaning products.

To illustrate the method of the invention the lard dispersion capacity of a surfactant under automatic dishwashing conditions and the lard dispersion capacity of a dishwashing detergent product using obscuration are detailed hereinbelow. Obscuration is defined as the amount of laser light blocked and scattered by the particles comprised in a dispersion. i.e., the amount of light that is not transmitted through the dispersion. Thus, the higher the obscuration the better is the soil dispersing, and in particular grease dispersing capacity, of the surfactant. In order to subject the surfactant to similar conditions to those found in a dishwasher, a solution comprising the surfactant is subjected to a temperature profile ramping from 30° C. to 50° C. and ending at 20° C. Meaningful points in order to understand the soil (in particular grease) suspending capacity of a surfactant are 36° C. (close to the lard solidification point) and 20° C., that is usually the lowest temperature achieved during the discharge of the dishwashing liquor.
Obscuration Measurement An aqueous solution comprising a surfactant is prepared. Dyed lard is added to this solution to form a mixture. This mixture is in the form of a dispersion. The obscuration resulting from this dispersion is measured vs time and temperature.

The surfactant solution is prepared by making 625 ml of a solution comprising 250 ppm of surfactant in deionised water, 574 ppm of sodium carbonate and 1896 ppm of sodium tripolyphosphate (the carbonate and phosphate are added to simulate the ionic strength of a dishwashing detergent typical formulation).

In the case of an automatic dishwashing product a solution is prepared comprising the finished product (rather than just the surfactant). The resulting solution is filtered to get rid of insoluble material.

The lard is prepared by mixing equal amounts of lard (unsalted lard) supplied from four different supermarkets (for example, Asda, Tesco, Morrison and Sainsbury in the UK). The lard preferably has a solidification temperature in the range of from about 36° C. to about 45° C. 0.1% w/w of Sudan III Red dye is added to the mixture. The dyed lard is gently heated and then placed into an oven at 50° C. before 0.75 g is added to the surfactant solution.

Obscuration is defined as a zero angle turbidity measurement which quantifies the amount of laser light blocked and scattered by the particles present in a dispersion. i.e., the amount of light that is not transmitted through the dispersion. It is akin to absorbance in the case of a spectrophotometer and is directly and linearly proportional to sample concentration.

The obscuration of the surfactant/lard dispersion is measured using a laser diffraction particle sizing instrument (Mastersizer 2000 from Malvern Instruments). The instrument is connected to a jacketed beaker containing the dispersion to be measured (surfactant/lard). The dispersion is recirculated between the beaker and the sampling cell of the particle sizing instrument where the obscuration is measured.

The jacketed beaker is connected to a thermostatic water bath to control the temperature of the suspension. The initial temperature of the dispersion is 30° C. Then a ramp is commenced where the temperature is taken up to 50° C. (this usually takes about 16 minutes) the dispersion is then cooled to 20° C. (this usually takes about 1 hour and 45 minutes). The heating and cooling rates are substantially linear, preferably linear. Preferably the heating rate is about 1.25° C./min and the cooling rating is about 0.3° C./min. This temperature cycle simulates the working conditions inside an automatic dishwasher.

Detailed Protocol to Measure Obscuration

The equipment used include: a laser diffraction particle sizing instrument Malvern Mastersizer 2000; a wet dispersion system equipped with an impeller (Malvern Hydro 2000MU) and a jacketed beaker; a thermostatic water bath (e.g. Lauda Ecoline RE320) to feed the jacket of the jacketed beaker and regulate actual sample temperature via an external Pt100 thermocouple with PID feedback loop; and a means of supplementing the water bath cooling rate to achieve the desired cooling ramp target (e.g. Haake EK20 refrigerated immersion coil cooler, frozen "cool packs" or similar).

The following steps are used to measure the obscuration of a surfactant/lard system:

1. Switch on Mastersizer 2000 and open software. Allow 30 minute warm up period for laser stabilisation, prior to commencing measurements.
2. 625 ml of the surfactant solution are transferred to the jacketed beaker.
3. The impeller unit is placed into the centre of the jacketed beaker.
4. Stirring at 1400 rpm is started.
5. The surfactant solution is circulated around the measurement cell to equilibrate its temperature with the surfactant solution.
6. Stirring is stopped and started again at 1400 rpm (to facilitate removal of any unwanted air in the system).
7. The speed of the stirrer is increased to 2000 rpm.
8. A thermocouple is inserted into the jacketed beaker.
9. The sample is left to equilibrate at 30° C.
10. When 30° C. is reached the 0.75 g of melted lard is injected into the centre of the beaker and obscuration measurement is commenced.
11. Immediately after, heating of the water bath from 30° C. to 50° C. is commenced (this takes about 16 minutes).
12. When 50° C. is reached, the water bath is immediately adjusted to cool the sample down to 20° C. (this takes about 1 hour and 45 minutes).

FIG. 1 shows the obscuration of 417 ppm Brij 30 (2-(dodecyloxy) ethanol available from Aldrich) in the presence of 0.75 g of lard in the presence of 574 ppm of sodium carbonate and 1896 ppm of sodium tripolyphosphate.

A calibration curve is used to find out the relationship between obscuration and the level lard dispersed.

To measure the obscuration of an automatic dishwashing product the method is as described above but the surfactant is replaced by the automatic dishwashing product. To create the solution the product is placed in a beaker with 5 liter of distilled water at 50° C., the product is left to dissolve for a period of 60 minutes, stifling at 300 rpm without heating (thus allowing the solution to cool from 50° C. to around 35° C. at the end of the 60 minutes). After 60 minutes the resulting solution is filtered using a vacuum pump and Hartley funnel to pass the liquor through a Whatman GF/C (coarse) glass microfiber filter. The filtrate is collected and vacuum filter a second time, using a Whatman GF/F (fine) glass microfiber filter.

Referring to FIG. 1, an example of the obscuration of 417 ppm of Brij 30 in the presence of 574 ppm of sodium carbonate and 1896 ppm of sodium tripolyphosphate is shown.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A method for quantifying the soil dispersion capacity of a cleaning product or component thereof where the method comprises the following steps:

a) making a solution comprising the cleaning product or component thereof, the solution being contained in a temperature controlled vessel;
b) adding the soil to the cleaning product or component thereof solution to form a mixture;
c) measuring the light blocked by the mixture at an initial temperature of 30° C.;
d) increasing the temperature of the mixture to about 50° C. and measuring the light blocked by the mixture at 50° C.; and
e) decreasing the temperature of the mixture to about 20° C. and measuring the light blocked by the mixture at 20° C.;
wherein the light blocked by the mixture is quantified by measuring obscuration using a particle size analyzer.

2. A method according to claim 1 comprising the additional step of insoluble separation from the solution of step a).

3. A method according to claim 1 comprising the step of measuring the light blocked by the solution of step a) and subtracting it to the light blocked by the mixture formed in step b).

4. A method according to claim 1 wherein the light blocked by the mixture is measured under simulated appliance conditions.

5. A method according to claim 1 wherein the temperature controlled vessel is a jacketed vessel.

6. A method according to claim 1 wherein the soil is grease or any particulate soil.

7. A method according to claim 1 wherein the cleaning product component is a surfactant or a surfactant system.

* * * * *